US009370328B2

(12) United States Patent
Eary et al.

(10) Patent No.: US 9,370,328 B2
(45) Date of Patent: Jun. 21, 2016

(54) METHODS AND SYSTEMS FOR DETERMINING TUMOR BOUNDARY CHARACTERISTICS

(71) Applicant: University of Washington through its Center for Commercialization, Seattle, WA (US)

(72) Inventors: Janet F. Eary, Seattle, WA (US); Todd L. Richards, Kenmore, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 78 days.

(21) Appl. No.: 14/091,124

(22) Filed: Nov. 26, 2013

(65) Prior Publication Data
US 2014/0148679 A1 May 29, 2014

Related U.S. Application Data

(60) Provisional application No. 61/731,138, filed on Nov. 29, 2012.

(51) Int. Cl.
*G06K 9/00* (2006.01)
*A61B 5/00* (2006.01)
*G06T 7/00* (2006.01)

(52) U.S. Cl.
CPC .............. *A61B 5/4887* (2013.01); *A61B 5/743* (2013.01); *G06T 7/0012* (2013.01); *G06T 7/0083* (2013.01); *G06T 2207/10088* (2013.01); *G06T 2207/30096* (2013.01)

(58) Field of Classification Search
None
See application file for complete search history.

(56) References Cited

U.S. PATENT DOCUMENTS 5,817,019 A * 10/1998 Kawashima ............. A61B 8/14
128/916
6,309,353 B1 10/2001 Cheng
6,891,964 B2 * 5/2005 Doi ....................... G06T 7/0012
382/131

(Continued)

FOREIGN PATENT DOCUMENTS

JP 2002291750 10/2002

OTHER PUBLICATIONS

Sachdeva et al., "A novel content-based active contour model for brain tumor segmentation", Magnetic Resonance Imaging, vol. 30, issue 5, Jun. 2012, pp. 694-715.*

(Continued)

Primary Examiner — Soo Jin Park
(74) Attorney, Agent, or Firm — McDonnell Boehnen Hulbert & Berghoff LLP

(57) ABSTRACT

Described herein are methods and systems for determining tumor boundary characteristics. One example method involves (a) receiving imaging data, wherein the imaging data indicates a tumor and one or more tissues that surround the tumor; (b) determining one or more radial segments that extend from the tumor to the one or more surrounding tissues based on the imaging data, wherein the one or more radial segments each comprise one or more respective data points indicating signal intensity; (c) determining one or more respective tumor boundary parameters for each of the one or more radial segments based on at least the one or more respective data points indicating signal intensity; (d) determining a tumor margin based on the one or more determined tumor boundary parameters; and (e) causing a graphical representation of the determined tumor margin to be displayed on a graphical display.

33 Claims, 12 Drawing Sheets

(56) References Cited

U.S. PATENT DOCUMENTS

| | | | |
|---|---|---|---|
| 7,233,687 B2 | 6/2007 | Ashton | |
| 7,418,123 B2* | 8/2008 | Giger | G06T 7/0012 382/132 |
| 7,466,848 B2* | 12/2008 | Metaxas | A61B 5/055 382/128 |
| 8,180,133 B2* | 5/2012 | Omi | G06T 7/0083 378/4 |
| 8,290,227 B2* | 10/2012 | Chen | G06T 7/0012 382/128 |
| 8,374,892 B2* | 2/2013 | Chang | A61B 8/08 382/128 |
| 8,559,689 B2* | 10/2013 | Mizuno | G06T 7/0014 382/128 |
| 9,076,222 B2* | 7/2015 | Bal | G06T 7/0083 |
| 2006/0025667 A1 | 2/2006 | Ashton | |
| 2006/0184043 A1 | 8/2006 | Tromberg | |
| 2008/0015448 A1 | 1/2008 | Keely | |
| 2009/0148007 A1 | 6/2009 | Zhao | |
| 2009/0202119 A1 | 8/2009 | Hefti | |
| 2009/0221920 A1 | 9/2009 | Boppart | |
| 2010/0104513 A1 | 4/2010 | Rittscher | |
| 2010/0316268 A1* | 12/2010 | Liang | G06T 19/00 382/128 |
| 2011/0176108 A1* | 7/2011 | Nakagawa | G06T 7/0083 351/206 |
| 2011/0181614 A1* | 7/2011 | Chang | G06T 7/0012 345/595 |
| 2012/0155734 A1* | 6/2012 | Barratt | G06T 7/0032 382/131 |
| 2013/0038707 A1* | 2/2013 | Cunningham | H04N 7/183 348/65 |
| 2015/0078641 A1* | 3/2015 | Tan et al. | 382/131 |

OTHER PUBLICATIONS

Eichelberger et al., "Maximum tumor diameter is an independent predictor of prostate-specific antigen recurrence in prostate cancer", Modern Pathology (2005) 18, 886-890.*
Allen SO, Moskovic EC, Fisher C et al. Adult rhabdomyosarcoma: cross-sectional imaging findings including histopathologic correlation. AJR Am J Roentgenol 2007; 189 (2):371-7.
Barile A, Zugaro L, Catalucci A et al. Soft tissue liposarcoma: histological subtypes, MRI and CT findings. Radiol Med 2002; 104 (3):140-9.
Collins MS, Koyama T, Swee RG et al. Clear cell chondrosarcoma: radiographic, computed tomographic, and magnetic resonance findings in 34 patients with pathologic correlation. Skeletal Radiol 2003; 32 (12):687-94.
Dim DC, Cooley LD, Miranda RN. Clear cell sarcoma of tendons and aponeuroses: a review. Arch Pathol Lab Med 2007; 131 (1):152-6.
Donmez FY, Tuzun U, Basaran C et al. MRI findings in parosteal osteosarcoma: correlation with histopathology. Diagn Intery Radiol 2008; 14 (3):142-52.
Eary JF, Conrad EU. Positron emission tomography in grading soft tissue sarcomas. Semin Musculoskelet Radiol 1999; 3:135-8.
Eary JF, Mankoff DA. Tumor metabolic rates in sarcoma using FOG PET. J Nucl Med 1998; 39:250-4.
Elias DA, White LM, Simpson OJ et al. Osseous invasion by soft-tissue sarcoma: assessment with MR imaging. Radiology 2003; 229 (1):145-52.
Fernebro J, Wiklund M, Jonsson K et al. Focus on the tumour periphery in MRI evaluation of soft tissue sarcoma: infiltrative growth signifies poor prognosis. Sarcoma 2006; 2006:21251.
Folpe AL, Lyles RH, Sprouse JT et al. (F-18) fluorodeoxyglucose positron emission tomography as a predictor of pathologic grade and other prognostic variables in bone and soft tissue sarcoma. Clin Cancer Res 2000; 6:1279-87.
Furukawa R, Akahane M, Yamada H et al. Endometrial stromal sarcoma located in the myometrium with a low-intensity rim on T2-weighted images: report of three cases and literature review. J Magn Reson Imaging 2010; 31 (4):975-9.

Hartman RP, Sundaram M, Okuno SH et al. Effect of granulocyte-stimulating factorson marrow of adult patients with musculoskeletal malignancies: incidence and MRI findings. AJR Am J Roentgenol 2004; 183 (3):645-53.
Ishikawa M, Ishizuka 0, Nakayama T et al. Alveolar soft-part sarcoma of the retroperitoneum. Int J Urol 2006; 13 (10):1355-7.
Kumagai K, Tomita M, Nozaki Y et al. MRI findings of an inflammatory variant of well differentiated liposarcoma. Skeletal Radiol 2010; 39 (5):491-4.
Li WY, Brock P, Saunders DE. Imaging characteristics of primary cranial Ewing sarcoma. Pediatr Radiol 2005; 35 (6):612-8.
Lin PP, Pino ED, Normand AN et al. Periosteal margin in soft-tissue sarcoma. Cancer 2007; 109 (3):598-602.
Liu QY, Li HG, Chen JY et al. [Correlation of MRI features to histopathologic grade of soft tissue sarcoma]. Ai Zheng 2008; 27 (8):856-60.
Miyake M, Tateishi U, Maeda T et al. CT and MRI features of low-grade fibromyxoid sarcoma in the shoulder of a pediatric patient. Radiat Med 2006; 24 (7):511-4.
Murphey MD, Jelinek JS, Temple HT et al. Imaging of periosteal osteosarcoma: radiologic-pathologic comparison. Radiology 2004; 233 (1):129-38.
Murphey MD, wan Jaovisidha S, Temple HT et al. Telangiectatic osteosarcoma: radiologic-pathologic comparison. Radiology 2003; 229 (2):545-53.
Namimoto T, Yamashita Y, Awai K et al. Combined use of T2-weighted and diffusion weighted 3-T MR imaging for differentiating uterine sarcomas from benign leiomyomas. Eur Radiol 2009; 19 (11):2756-64.
Peersman B, Vanhoenacker FM, Heyman S et al. Ewing's sarcoma: imaging features. Jbr-Btr 2007; 90 (5):368-76.
Pilavaki M, Drevelegas A, Nenopoulou H et al. Foci of decreased signal on T2- weighted MR images in leiomyosarcomas of soft tissue: correlation between MR and histological findings. Eur J Radiol 2004; 51 (3):279-85.
Tanaka YO, Nishida M, Tsunoda H et al. Smooth muscle tumors of uncertain malignant potential and leiomyosarcomas of the uterus: MR findings. J Magn Reson Imaging 2004; 20 (6):998-1007.
Tateishi U, Hasegawa T, Nojima T et al. MRI features of extraskeletal myxoid chondrosarcoma. Skeletal Radiol 2006; 35 (1):27-33.
Varma DG. Imaging of soft-tissue sarcomas. Curr Oncol Rep 2000; 2 (6):487-90.
Eary JF, O'Sullivan F, O'Sullivan J, Conrad EU. Spatial heterogeneity in sarcoma 18F-FDG uptake as a predictor of patient outcome. J Nucl Med. Dec. 2008;49(12):1973-9.
O'Sullivan F, Roy S, Eary J. A statistical measure of tissue heterogeneity with application to 3D PET sarcoma data. Biostatistics. Jul. 2003;4(3):433-48.
O'Sullivan F, Roy S, O'Sullivan J, Vernon C, Eary J. Incorporation of tumor shape into an assessment of spatial heterogeneity for human sarcomas imaged with FOG-PET. Biostatistics. Apr. 2005;6(2):293-301.
Richards TL, Eary JF, O'Sullivan F, Conrad EU. A method for characterizing sarcoma tumour boundary scanned with T2-weighted MRI. J Biomed Graph Comput. Dec. 1, 2011;1(1):1-9.
McKee, M.D., et aL, The prognostic significance of margin width for extremity and trunk sarcoma. J Surg Oncol, 2004. 85(2): p. 68-76.
Gerrand, C. H., et aL, Classification of positive margins after resection of soft-tissue sarcoma of the limb predicts the risk of local recurrence. J Bone Joint Surg Br, 2001. 83(8): p. 1149-55.
Kim, Y.B., et aL, Clinical significance of margin status in postoperative radiotherapy for extremity and truncal soft-tissue sarcoma. Int J Radiat Oncol Bioi Phys, 2008. 70(1): p. 139-44.
Zagars, G.K., et aL, Surgical margins and reresection in the management of patients with soft tissue sarcoma using conservative surgery and radiation therapy. Cancer, 2003. 97(10): p. 2544-53.
Liu, Q.Y., et aL, [Correlation of MRI features to histopathologic grade of soft tissue sarcoma]. Ai Zheng, 2008. 27(8): p. 856-60.
Carano, R.A., et aL, Quantification of tumor tissue populations by multispectral analysis. Magn Reson Med, 2004. 51 (3): p. 542-51.

* cited by examiner

METHODS AND SYSTEMS FOR DETERMINING TUMOR BOUNDARY CHARACTERISTICS

RELATED APPLICATIONS

This application claims priority to U.S. Provisional Patent Application Ser. No. 61/731,138 filed Nov. 29, 2012, entitled Software and Method for Application to Surgical Navigation Systems, which is incorporated herein in its entirety.

STATEMENT OF U.S. GOVERNMENT INTEREST

This invention was made with government support under grant no. R01CA065537-14, awarded by the National Institutes of Health. The government has certain rights in the invention.

BACKGROUND

Unless otherwise indicated herein, the materials described in this section are not prior art to the claims in this application and are not admitted to be prior art by inclusion in this section.

Tumor resection has long been a mainstay of treatment for many kinds of cancers, such as sarcoma. For example, while many treatment protocols for sarcoma involve neo-adjuvant treatment with chemotherapy and radiation, a leading mode of sarcoma treatment in adults and children is primary tumor resection. The goals of resection include removal of the primary tumor to prevent local recurrence and metastases, preservation of normal tissue function, and in the majority of cases, preservation of skeletal and limb function. Tumor resection may also be a mode of treatment for other types of tumors.

In planning for tumor resection surgery, surgeons may consult images of the tumor that are produced using medical imaging techniques such as magnetic resonance imaging (MRI), positron emission tomography (PET), and computed tomography (CT). These images of the tumor show the boundary between the tumor and the surrounding normal tissue. Often, the boundary between the tumor and surrounding tissue is not well-defined. Instead, the tumor infiltrates into the surrounding tissue. Therefore, since leaving tumor mass in the body is associated with poor patient outcome, surgeons try to remove the tumor along with some surrounding tissue in an attempt to have no tumor left behind in the body.

To determine whether tumor was left behind in the body, a pathologist may examine and sample the edge of the removed tumor to determine if the tumor involves the surface (margins) of the specimen. The cut surface of the tissue mass (tumor and normal tissue) removed may be referred to as the "tumor margin." When the entire tumor is removed with a generous covering of normal tissue on all surfaces, then the tumor resection specimen is said to be negative, or margins free of tumor. If the tumor is present at the edge of the mass, then the margins are said to be positive, or tumor involved. This implies that tumor is left behind in the body at these locations and the patient is at high risk for tumor re-growth (local recurrence) and shortened survival.

Often, tumor resection surgery is performed with a goal of a resected tumor that has negative margins. However, in some circumstances, surgery will result in a tumor with positive margins since the tumor sometimes infiltrates into the surrounding tissue making it difficult to determine the tumor boundary. In other circumstances, positive margins are a planned result of the surgery. For example, in sarcoma, because there is often little normal tissue surrounding the tumor, resection margins can have tumor 1-2 mm from the edge of the resection and are called "marginal" margins. Although a lack of tumor margin involvement in these types of resection cannot be assumed, tumor resections with marginal margins are sometimes performed to preserve a limb when amputation would otherwise be the alternative, among other situations.

While marginal margins cannot be avoided in every surgery, not all marginal margins are equal. By better understanding the nature of the tumor boundary, the marginality of the tumor margin can be reduced.

SUMMARY

Described herein are methods and systems for determining tumor boundary characteristics. Such methods and systems may involve quantitatively determined tumor boundary parameters that can be used to infer various tumor boundary characteristics. These tumor boundary characteristics can aid in pre-surgery planning and predication of local tumor recurrence, among other benefits. In addition, the quantitative characterization described in this application may be combined with qualitative characterization.

The method and system may apply to a broad range of tumor types, such as sarcoma and carcinoma, and has been demonstrated on the following tumor types: serous carcinoma, leiomysarcoma, synovial sarcoma, alveolar, rhabomyosarcoma, pleomorphic sarcoma, liposarcoma, osteosarcoma, desmoplastic round cell, chondrosarcoma, Ewing's sarcoma, myxofibrosarcoma, synovial sarcoma, and spindle cell sarcoma.

In one aspect, a computer-implemented method is provided. The method may involve: (1) receiving imaging data, wherein the imaging data indicates a tumor and one or more tissues that surround the tumor; (2) determining one or more radial segments that extend from the tumor to the one or more surrounding tissues based on the imaging data, where the one or more radial segments each comprise one or more respective data points indicating signal intensity; (3) determining one or more respective tumor boundary parameters for each of the one or more radial segments based on at least the one or more respective data points indicating signal intensity, where each of the one or more radial segments intersect a tumor boundary; (4) determining a tumor margin based on the one or more determined tumor boundary parameters; and (5) causing a graphical representation of the determined tumor margin to be displayed on a graphical display.

In a further aspect, a physical computer-readable medium is provided. The physical computer-readable medium may include instructions that are executable by a computing device to cause the computing device to perform functions. The functions include: (1) receiving imaging data, where the imaging data indicates a tumor and one or more tissues that surround the tumor; (2) determining one or more radial segments that extend from the tumor to the one or more surrounding tissues based on the imaging data, where the one or more radial segments each comprise one or more respective data points indicating signal intensity; (3) determining one or more respective tumor boundary parameters for each of the one or more radial segments based on at least the one or more respective data points indicating signal intensity, where each of the one or more radial segments intersect a tumor boundary; (4) determining a tumor margin based on the one or more determined tumor boundary parameters; and (5) causing a graphical representation of the determined tumor margin to be displayed on a graphical display.

In a further aspect, a computing device is provided. The computing device may include: (A) a display; (B) a physical, non-transitory computer readable medium; and (C) program instructions stored on the physical computer readable medium and executable by at least one processor to cause the computing device to: (1) receive imaging data, where the imaging data indicates a tumor and one or more tissues that surround the tumor; (2) determine one or more radial segments that extend from the tumor to the one or more surrounding tissues based on the imaging data, where the one or more radial segments each comprise one or more respective data points indicating signal intensity; (3) determine one or more respective tumor boundary parameters for each of the one or more radial segments based on at least the one or more respective data points indicating signal intensity, where each of the one or more radial segments intersect a tumor boundary; (4) determine a tumor margin based on the one or more determined tumor boundary parameters; and (5) cause a graphical representation of the determined tumor margin to be displayed on a graphical display.

These as well as other aspects, advantages, and alternatives, will become apparent to those of ordinary skill in the art by reading the following detailed description, with reference where appropriate to the accompanying drawings.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that aspects of the present disclosure, as generally described herein, and illustrated in the figures, can be arranged, substituted, combined, separated, and/or designed in a wide variety of different configurations, all of which are explicitly contemplated herein.

1. Example Architecture

Figure 1:
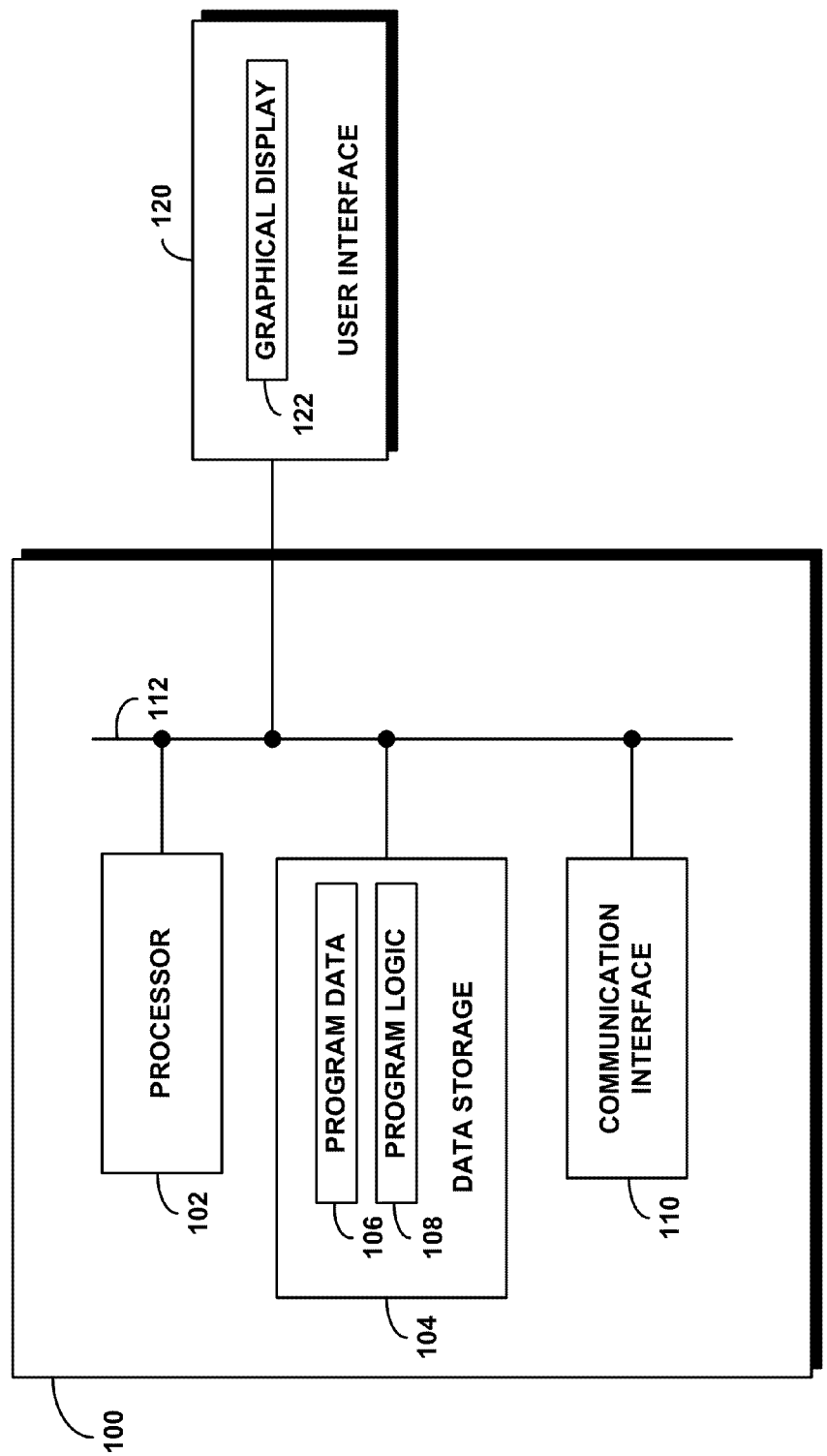
FIG. 1 shows a simplified block diagram of a computing device, in accordance with an example embodiment.

FIG. 1 shows a simplified block diagram of an example computing device 100 in which the present method can be implemented. It should be understood that this and other arrangements described herein are set forth only as examples. Those skilled in the art will appreciate that other arrangements and elements (e.g., machines, interfaces, functions, orders, and groupings of functions, etc.) can be used instead and that some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. And various functions described herein may be carried out by a processor executing instructions stored in memory.

As shown in FIG. 1, computing device 100 may include processor 102, data storage 104, and communication interface 110, all linked together via system bus, network, or other connection mechanism 112.

Processor 102 may include one or more general purpose microprocessors and/or one or more dedicated signal processors and may be integrated in whole or in part with communication interface 110. Data storage 104 may include memory and/or other storage components, such as optical, magnetic, organic or other memory disc storage, which can be volatile and/or non-volatile, internal and/or external, and integrated in whole or in part with processor 102. Data storage 104 may be arranged to contain (i) program data 106 and (ii) program logic 108. Although these components are described herein as separate data storage elements, the elements could just as well be physically integrated together or distributed in various other ways. For example, program data 106 may be maintained in data storage 104 separate from program logic 108, for easy updating and reference by program logic 108.

Communication interface 110 typically functions to communicatively couple computing device 100 to networks. As such, communication interface 110 may include a wired (e.g., Ethernet) and/or wireless (e.g., Wi-Fi) packet-data interface, for communicating with other devices, entities, and/or networks. Computing device 100 may also include multiple interfaces 110, such as one through which computing device 100 sends communication, and one through which computing device 100 receives communication.

Computing device 100 may also include, or may be otherwise communicatively coupled to, user interface 120. User interface 120 may include one or more elements for communicating outputs, for example, one or more graphical displays 122 and/or a speaker. In operation, user interface 120 may be configured to display a graphical user interface (GUI) via graphical display 122, corresponding to use of such a GUI.

Figure 2:
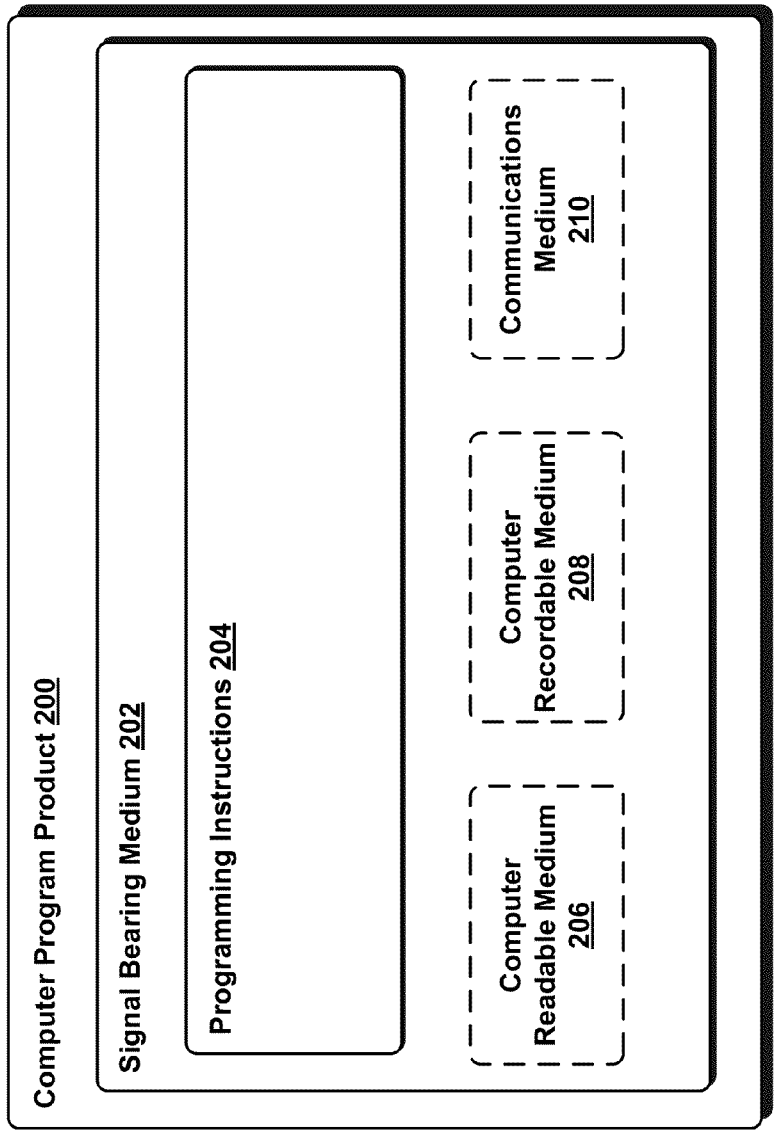
FIG. 2 shows an illustrative computer-readable medium, in accordance with an example embodiment.

As noted above, in some embodiments, the disclosed methods may be implemented by computer program instructions encoded on a physical, and/or non-transitory, computer-readable storage media in a machine-readable format, or on other non-transitory media or articles of manufacture. FIG. 2 is a schematic illustrating a conceptual partial view of an example computer program product that includes a computer program for executing a computer process on a computing device, arranged according to at least some embodiments presented herein.

In one embodiment, the example computer program product 200 is provided using a signal bearing medium 202. The signal bearing medium 202 may include one or more programming instructions 204 that, when executed by one or more processors may provide functionality or portions of the functionality described herein. In some examples, the signal bearing medium 202 may encompass a computer-readable medium 206, such as, but not limited to, a hard disk drive, a Compact Disc (CD), a Digital Video Disk (DVD), a digital tape, memory, etc. In some implementations, the signal bearing medium 202 may encompass a computer-recordable medium 208, such as, but not limited to, memory, read/write (R/W) CDs, R/W DVDs, etc. In some implementations, the signal bearing medium 202 may encompass a communications medium 210, such as, but not limited to, a digital and/or an analog communication medium (e.g., a fiber optic cable, a waveguide, a wired communications link, a wireless communication link, etc.). Thus, for example, the signal bearing medium 202 may be conveyed by a wireless form of the communications medium 210. It should be understood, however, that computer-readable medium 206, computer recordable medium 208, and communications medium 210 as contemplated herein are distinct mediums and that, in any event, computer-readable medium 208 is a physical, non-transitory, computer-readable medium.

The one or more programming instructions 204 may be, for example, computer executable and/or logic implemented instructions. In some examples, a computing device such as the computing device 100 of FIG. 1 may be configured to provide various operations, functions, or actions in response to the programming instructions 204 conveyed to the computing device 100 by one or more of the computer readable medium 206, the computer recordable medium 208, and/or the communications medium 210.

2. Example Method

Figure 3:
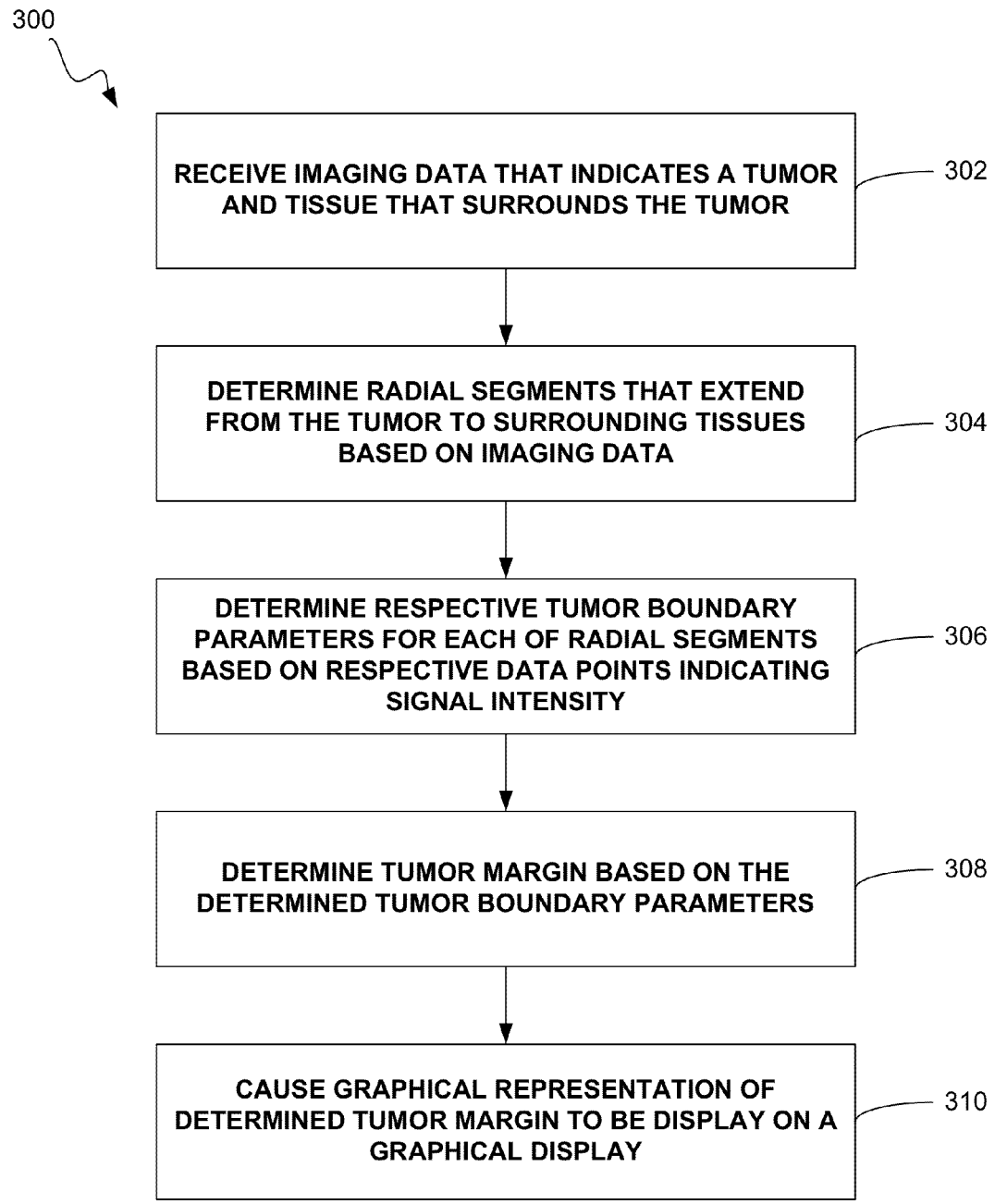
FIG. 3 shows an illustrative method for determining tumor boundary parameters.

FIG. 3 shows a flowchart depicting functions that can be carried out in accordance with at least one embodiment of an example method. As shown in FIG. 3, method 300 begins at block 302 with a computing device receiving imaging data, wherein the imaging data indicates a tumor and one or more tissues that surround the tumor. At block 304, the computing device determines one or more radial segments that extend from the tumor to the one or more surrounding tissues based on the imaging data, where the one or more radial segments each comprise one or more respective data points indicating signal intensity, where each of the one or more radial segments intersect a tumor boundary. At block 306, the computing device determines one or more respective tumor boundary parameters for each of the one or more radial segments based on at least the one or more respective data points indicating signal intensity. At block 308, the computing device determines a tumor margin based on the one or more determined tumor boundary parameters. And, at block 310, the computing device causes a graphical representation of the determined tumor margin to be displayed on a graphical display.

In some implementations, method 300 may be carried out entirely, or in part, by computing device 100, or some other computing system.

a. Receive Imaging Data

At block 302, a computing device receives imaging data, where the imaging data indicates a tumor and one or more tissues that surround the tumor. For example, computing device 100 in FIG. 1 may receive the imaging data over system bus, network, or other connection mechanism 112. In some embodiments, the computer device may receive the imaging data from a medical imaging machine, such as a magnetic resonance imaging (MRI) machine, a positron emission tomography (PET) machine, or a computed tomography (CT) machine. In other embodiments, the computing device may receive the imaging data from another computing device via a network. In some embodiments, the computing device may receive the imaging data via a transfer from a data storage device, such as a hard disk drive or a USB flash drive. In other embodiments, the computing device may receive the imaging data via a transfer from a data storage medium, such as a CD-ROM disk. Many other examples are possible as well.

The imaging data may include one or more medical images that show an image of the human body (or a part thereof). Such medical images may be created using one or more of a variety of medical imaging techniques, such as magnetic resonance imaging (MRI), positron emission tomography (PET), and computed tomography (CT). Other types of medical images are contemplated as well, such as ultrasound, tactile imaging, or photoacoustic imaging, among other possibilities.

The one or more medical images may include one or more three-dimensional medical images. In some embodiments, a three-dimensional (3-d) medical image may be created by combining multiple two-dimensional (2-d) scans as layers to form a three-dimensional image. In other embodiments, the medical imaging machine produces a three-dimensional medical image.

As noted, the imaging data indicates a tumor and one or more tissues that surround the tumor. The tumor (or neoplasm) may include different types of tumors, such as sarcomas or carcinomas. The surrounding tissue may include any tissue that completely or partially surrounds the tumor. The interface between the tumor and the surrounding tissue may be referred to as a tumor boundary. In some embodiments, the imaging data includes in vivo imaging data for a patient.

In some embodiments, the imaging data includes at least one MR image. One or more MR images collected during a session may be referred to as a scan. In some circumstances, MR techniques may be chosen because they are capable of producing relatively higher-resolution and higher-detailed soft tissue images as compared with other medical imaging techniques. In addition, MR techniques are capable of producing 3-d images that can image a tumor in three dimensions. In other circumstances, different imaging techniques may be preferred. Such imaging techniques may, in some circumstances, produce relatively higher-resolution and higher-detailed images.

In some embodiments, the imaging data indicates signal intensity. An MR image may have a pixel resolution, such as 512 pixels by 512 pixels, for a two-dimensional MR image. Or, where the MR image is 3-d, the MR image may have a voxel resolution, such as 512 voxels by 512 voxels by 66 voxels. The terms pixels and voxels may be used interchangeably, such that description applying to pixels for 2-d images applies to voxels for 3-d images, and vice-versa.

A pixel may represent a physical region within the MR image. For example, a pixel may represent a physical region of 0.8×0.8 mm. Therefore, the pixel is an approximation of that physical region. Likewise, a voxel may define a physical volume; for example, a volume of 0.8×0.8×7 mm. Because each pixel is an approximation of a physical region, each pixel may have a physical location. Such a physical location may be represented by a 2-d or 3-d coordinate system.

Each pixel (or voxel, as noted above) in an MRI image may have a signal intensity sample (or simply, signal intensity) associated with that respective pixel. The signal intensity associated with that respective pixel represents the amplitude of the RF signal at one point. However, it should be understood that a pixel is an approximation of a region. Therefore, the imaging data may be a 2-d or 3-d array of signal intensity data. Such an array may be referred to as an image matrix. Depending on the imaging sequence used, the MRI signal intensity may indicate a free water density or levels of contrast density, among other alternatives. In MR images, different tissues in the MR image may appear lighter or darker, depending on the signal intensity of the imaged tissues.

In some embodiments, MR images that have a certain quality threshold are chosen for use in connection with block 302. For example, MR images having a signal-to-noise (SNR) ratio of above 30 may be chosen.

In some embodiments, the MR images may be corrected and/or enhanced using one or more image analysis tools. Some examples include the FMRIB Software Library (FSL) from Oxford, UK and the Insight Segmentation and Registration Toolkit (ITK) from the National Library of Medicine.

In some embodiments, the imaging data includes at least one T2-weighted MR image. Under some circumstances, such as where the imaging data indicates a sarcoma, a T2-weighted image produces a relatively detailed representation of the tumor, tumor-involved, and normal surrounding tissue. This can apply to other types of tumors as well, and can be applied to the numerous types of tumors. In particular, T2-weighting may capture a relatively large difference in water mobility characteristics between tumor (such as sarcoma) and normal surrounding tissue.

Figure 4:
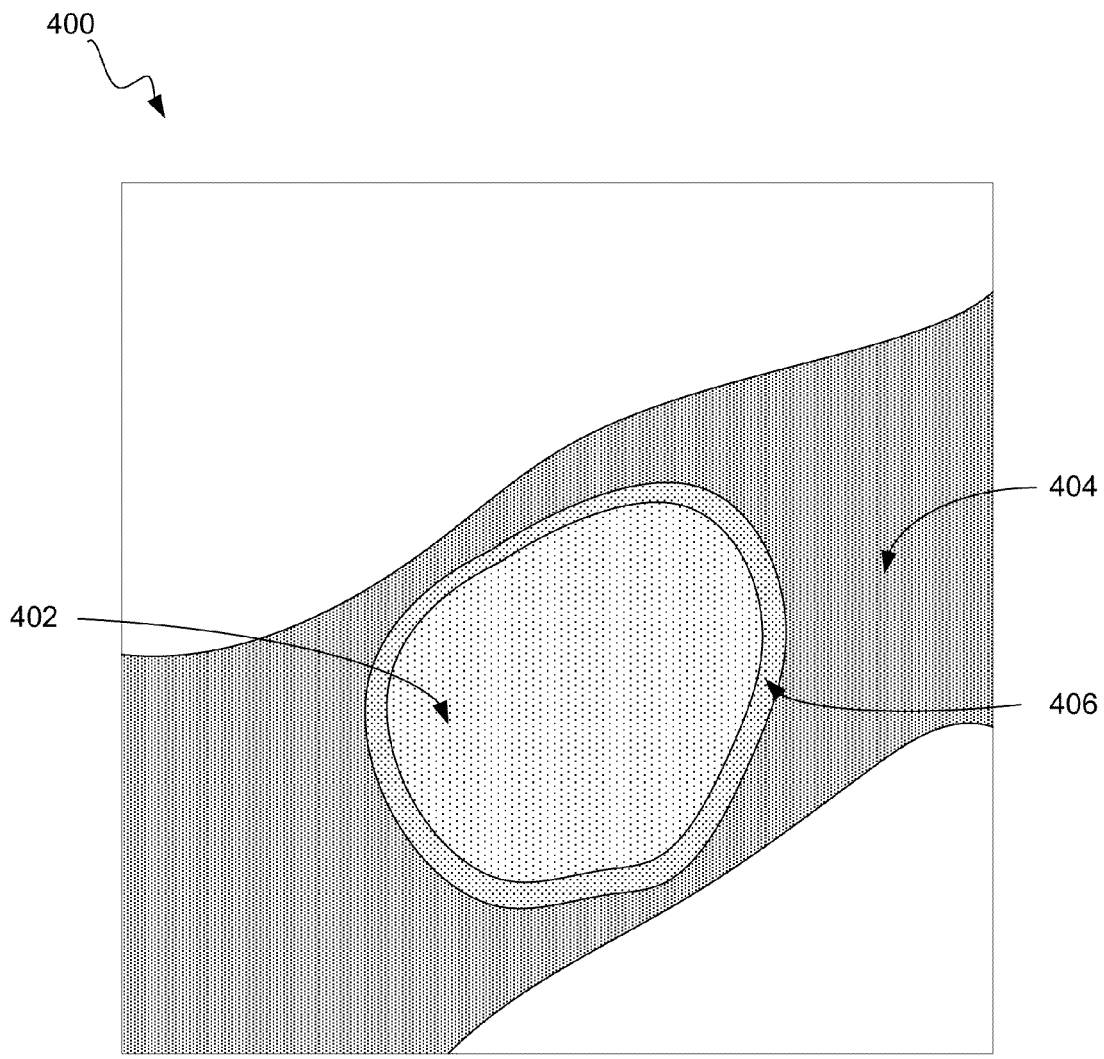
FIG. 4 shows an illustrative MR image of a tumor and surrounding tissue.

FIG. 4 depicts illustrative imaging data 400. Imaging data 400 is a representation of a 2-d T2-weighted MRI image. Imaging data 400 may represent one slice of a 3-d MR image. The MR image shows a sarcoma 402 and surrounding tissue 404. FIG. 4 also shows tumor-involved surrounding tissue 406. As noted above, T2-weighted MR images are indicative of the water mobility characteristics of the imaged tissue. In T2-weighted MR images, sarcomas may have higher signal intensity than the surrounding tissue because of the greater density of water in the tumor as compared to the surrounding tissue. As a result, sarcomas may appear lighter in T2-weighted MR images.

It should be understood that the particular imaging data (and elements thereof, including the tumor and surrounding tissue) shown in FIG. 4 is set forth for purposes of example and explanation only. Other examples of imaging data exist, and any such imaging data may be within the scope of the example method disclosed herein. The imaging data shown in FIG. 4 should not be taken to be limiting.

As noted above, the interface between the tumor and the surrounding tissue may be referred to as the tumor boundary. The computing device may define the tumor boundary by calculating a signal intensity threshold. For example, signal intensities above a certain signal intensity threshold may indicate the presence of tumor, while signal intensities below a certain threshold may indicate the presence of surrounding tissue. The signal intensity threshold may be statistically based on the average and standard deviation of both the signal intensities associated with the tumor shown in the imaging data and the signal intensities of the surrounding tissue. Other techniques to define the tumor boundary are possible as well.

i. Receiving Imaging Data in a First Study

A first study was conducted that involved twenty subjects having the following tumor types: serous carcinoma, leiomysarcoma, synovial sarcoma, alveolar, rhabomyosarcoma, pleomorphic sarcoma, liposarcoma, osteosarcoma, desmoplastic round cell, chondrosarcoma, Ewing's sarcoma, myxofibrosarcoma, synovial sarcoma, and spindle cell sarcoma. T2-weighted scans were acquired from the twenty subjects. The scans had been routinely collected as part of the clinical radiological protocol. The scans were acquired on three different MR scanner types including General Electric Signa Excite, Philips Medical Systems, and Siemens. The scans were acquired with the following parameters: (1) fast-spin echo type pulse sequences, (2) T2-weighted echo times ranging from 69 to 100 milliseconds, (3) repetition times ranging from 3000 to 5000 milliseconds, (4) field of view and scan resolution set to encompass the body part where the tumor was located, and (5) typical spatial matrix for acquisition was 512×512×66 voxels each with dimensions of 0.8×0.8×7 mm.

ii. Receiving Imaging Data in a Second Study

In a second study, thirty two subjects were involved. T2-weighted scans were acquired from the twenty subjects. The scans were acquired on three different MR scanner types including General Electric Signa Excite, Philips Medical Systems, and Siemens. The scans were acquired with the following parameters: (1) fast-spin echo type pulse sequences, (2) T2-weighted echo times ranging from 69 to 100 milliseconds, (3) repetition times ranging from 3000 to 5000 milliseconds, (4) field of view and scan resolution set to encompass the body part where the tumor was located, and (5) typical spatial matrix for acquisition was 512×512×66 voxels each with dimensions of 0.8×0.8×7 mm. Subject characteristics are shown in Table 1 below:

TABLE 1

Characteristics of Thirty Two Subjects

| Variable | Level | Frequency | Percentage |
|---|---|---|---|
| Sex | M | 17 | 53.1 |
|  | F | 15 | 46.9 |
| Metastatic disease at diagnosis? | Yes | 2 | 6 |
|  | No | 30 | 94 |
| Pre-study tumor grade | Low | 2 | 9.4 |
|  | Intermediate | 8 | 25 |
|  | High | 21 | 65.6 |
| Tumor subtype | Bone | 6 | 19 |
|  | Cartilage | 1 | 3 |
|  | Soft tissue | 25 | 78 | b. Determine Radial Segments that Extend from the Tumor to the Surrounding Tissues At block 304, the computing device determines one or more radial segments that extend from the tumor to the one or more surrounding tissues based on the imaging data. In some embodiments, the one or more radial segments each include one or more respective data points indicating signal intensity. In further embodiments, a number of the one or more radial segments is determined based on a determined degree of irregularity of the tumor boundary.

As described above, each pixel may have both a physical location and a signal intensity associated with the respective pixel. A number of pixels may be combined to form a radial segment that extends from the tumor to the one or more surrounding tissues. The path of the radial segment may be based upon the physical location of the pixels in the path. Since the pixels include a signal intensity, the radial segment represents a sequence of signal intensities that vary as the path of the radial segment crosses from tumor issue to the surrounding normal tissue.

Figure 5:
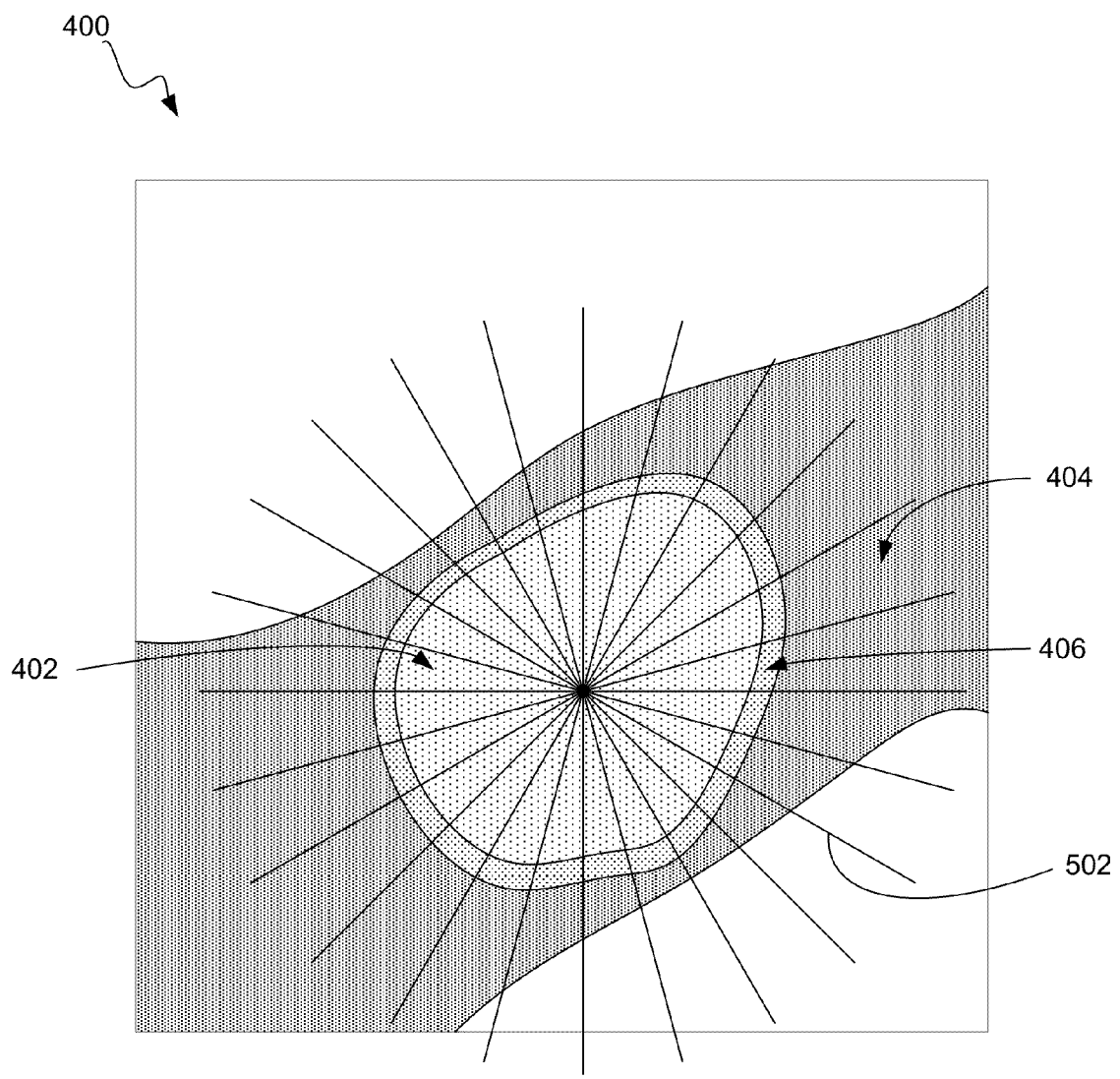
FIG. 5 shows illustrative radial segments overlaid onto an MR image of a tumor and surrounding tissue.

FIG. 5 depicts illustrative imaging data 400 that shows sarcoma 402, surrounding tissue 404, and tumor-involved surrounding tissue 406, as described in FIG. 4. In addition, FIG. 5 shows an illustrative radial segment 502, along with other radial segments, as shown. Radial segment 502 extends from the sarcoma 402, through the tumor-involved surrounding tissue 406, to the surrounding tissue 404. Radial segment 502 includes a number of pixels, each having a signal intensity value.

In some embodiments, the one or more radial segments may emanate from a point near the center of the tumor, as shown in FIG. 5. Such a point may be referred to as a tumor reference point. In some embodiments, the tumor reference point may be user-defined. Other embodiments in which the radial segments do not emanate from a single point are contemplated as well.

In other embodiments, the tumor reference point may be determined by the computing device. In such embodiments, before determining the one or more radial segments, the computing device may define a tumor reference point that is indicative of a center of the tumor based on the imaging data. The defined tumor reference point may be a statistically approximated center point based on the defined tumor boundary.

In further embodiments, the defined tumor reference point may be the centroid of the region defined by the defined tumor boundary. Some examples include determination of the centroid based on approximation of a finite set of points (e.g. pixels or voxels), such that the centroid of a finite set of k points $x_1, x_2, \ldots, x_k$ is $C=x_1+x_2+\ldots+x_k/k$. Other methods of calculating the centroid are possible as well.

Figure 8:
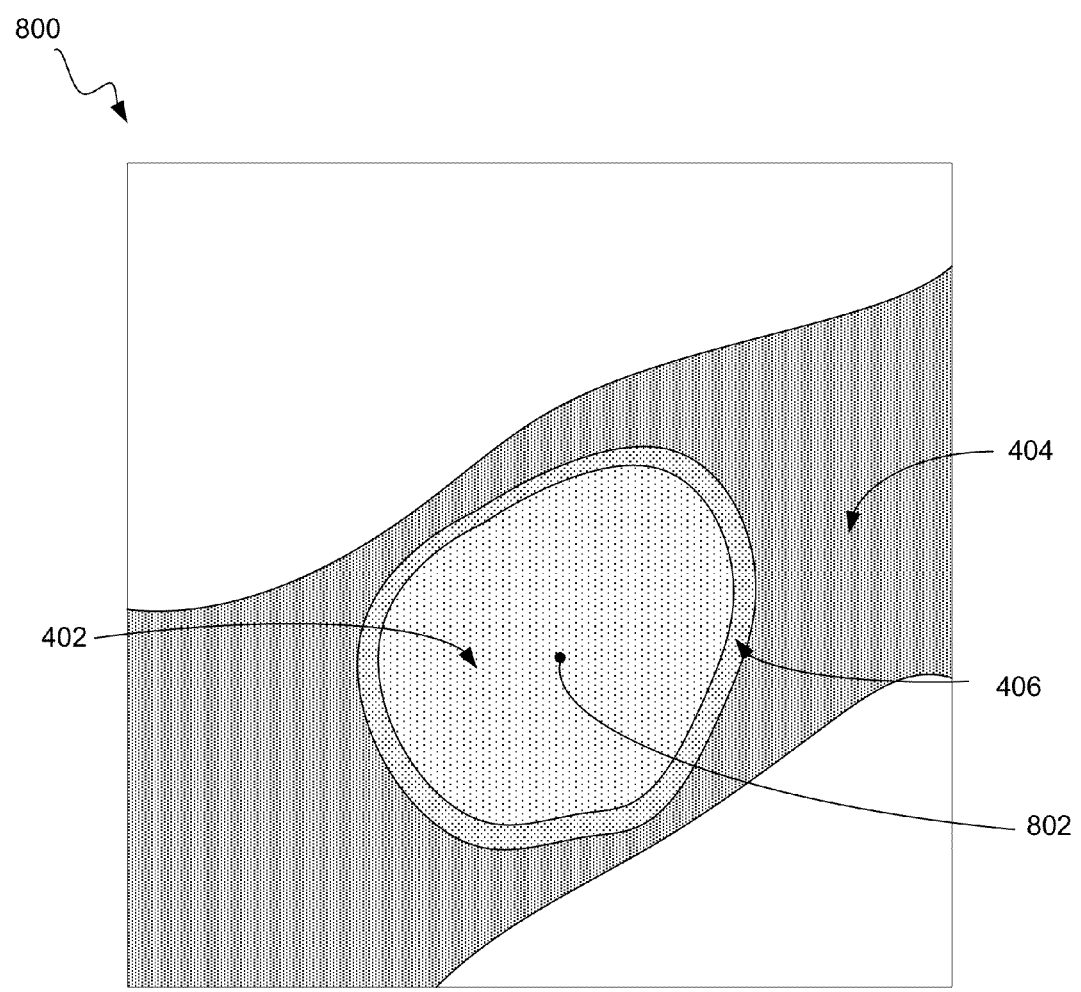
FIG. 8 shows an illustrative tumor reference point overlaid onto an MR image of a tumor and surrounding tissue.

FIG. 8 depicts illustrative imaging data 400 that shows a sarcoma 402, surrounding tissue 404, and tumor-involved surrounding tissue 406, as described in FIG. 4. In addition, FIG. 8 depicts a defined tumor reference point 802.

In some embodiments, the number of determined radial segments is predetermined. For example, ninety radial segments may be determined. The number of determined radial segments may be determined based on the desired compute time and the resolution of the imaging data, among other factors. A greater number of radial segments may increase the compute time involved in determining the radial segments, determining the tumor boundary characteristics, and determining the tumor margin. However, a greater number of radial segments may help to more accurately characterize the tumor boundary. But, the number of radial segments is limited by the resolution of the imaging data.

As one example embodiment, where the radial segments are determined for 2-d imaging data, the radial segments may be generated using the following equations:

$$x(\text{angle, segment\_length})=\text{cosine}(\text{angle})*\text{segment\_length}$$

$$y(\text{angle, segment\_length})=\text{cosine}(\text{angle})*\text{segment\_length}$$

In such equations, x represents the horizontal Cartesian coordinate (commonly x) in the same coordinate space as the imaging data and y represents the vertical Cartesian coordinate (commonly y) in the same coordinate space as the imaging data. To generate ninety radial segments, for example, the angle is incremented 90 times every 4 degrees for a total of 360 degrees and the segment_length variable is incremented in a loop for each pixel until the end of the radial segment is reached. This example may be repeated for each slice of 3-d imaging data. The above example is provided only for illustrative purposes. Many other techniques for generating the radial segments are possible.

In some embodiments, the computing device may determine the number of the one or more determined radial segments. To facilitate this determination, the computing device may determine a degree of irregularity of the tumor boundary. The computing device may determine the number of the determined one or more radial segments based on the determined degree of irregularity of the tumor boundary. For example, if a tumor boundary is more irregular, more radial segments may be used to characterize the tumor with sufficient accuracy. However, if the tumor boundary is less irregular, fewer radial segments may be used for sufficiently accurate characterization.

Figure 10A:
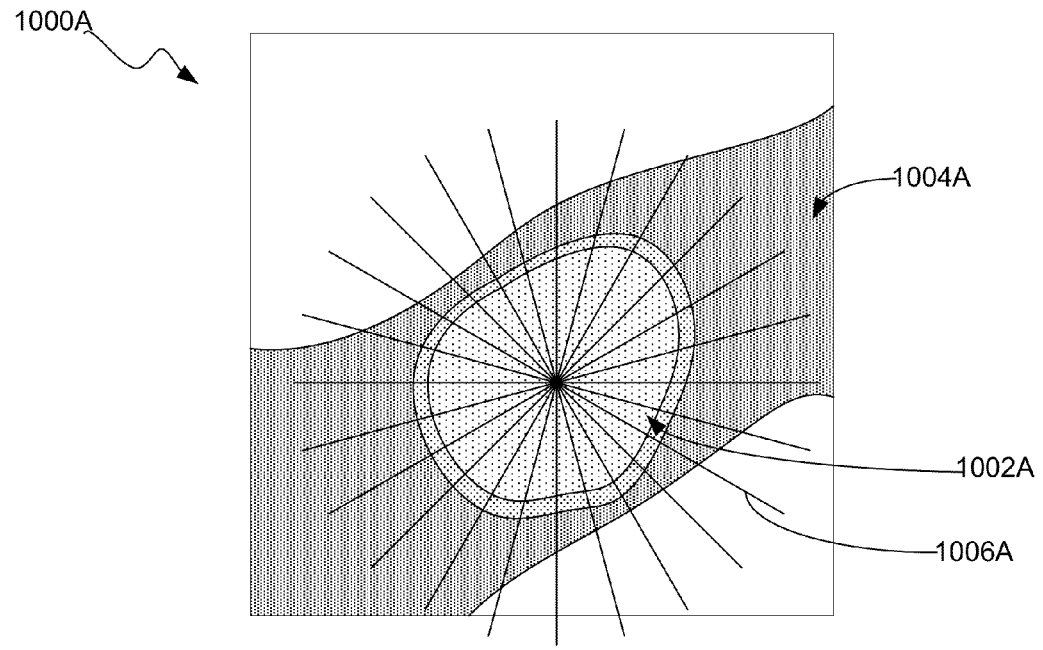
FIG. 10A shows a set of illustrative radial segments overlaid onto an MR image of a tumor and surrounding tissue, in an example embodiment.

FIG. 10A depicts imaging data 1000A that shows a tumor 1002A, surrounding tissue 1004A, and tumor-involved tissue 1006A. Tumor 1002A has a tumor boundary with the surrounding tissue that is relatively uniform. With such a tumor, fewer radial segments may be needed to characterize the tumor, as shown.

Figure 10B:
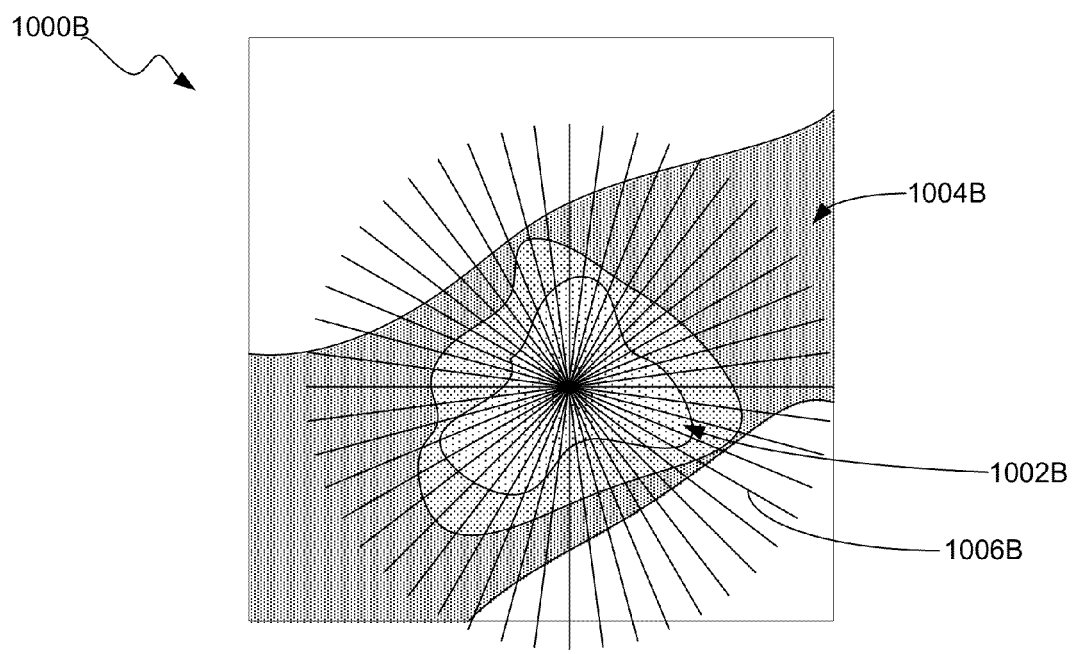
FIG. 10B shows another set of illustrative radial segments overlaid onto an MR image of a tumor and surrounding tissue, in an example embodiment.

FIG. 10B depicts imaging data 1000B that shows a tumor 1002B, surrounding tissue 1004B, and tumor-involved tissue 1006B. Tumor 1002B has a tumor boundary with the surrounding tissue that is relatively irregular. With such a tumor, more radial segments may be needed to characterize the tumor because the tumor boundary has irregular aspects, as shown.

One having skill in the art will appreciate that the imaging data may be manipulated such that equivalents to radial segments may be used. For example, the computing device may determine concentric rings that emanate from a point near the center of the tumor and continue to the surrounding tissue. Other examples are possible as well.

Returning to FIG. 5, in some embodiments, the radial segments may extend outside of the imaging data, as shown. As one example, this arrangement may occur when the tumor is not centered within the imaging data. Such portions of the radial segments may be assigned a default intensity value, such as 0, and may be disregarded in the image analysis. In other embodiments, the radial segment may end when the path of the radial segment reaches the boundaries of the imaging data.

c. Determine Respective Tumor Boundary Parameters for Each of the Radial Segments At block 306, the computing device determines one or more respective tumor boundary parameters for each of the one or more radial segments based on at least the one or more respective data points indicating signal intensity, wherein each of the one or more radial segments intersect a tumor boundary. Determining one or more respective tumor boundary parameters for each of the one or more radial segments may include determining, for each of the one or more respective radial segments, at least one of: (i) an average rate in change in signal intensity over the radial segment, (ii) a maximum rate in change in signal intensity over the radial segment, (iii) a normalized signal intensity at the tumor boundary; or (iv) a distance from the tumor boundary to the maximum signal intensity along the tumor margin within a predetermined distance.

To aid in the determination of the one or more respective tumor boundary parameters for each of the one or more radial segment, signal intensity along each radial segment may be plotted as a function of distance. This may indicate the details in how the signal intensity varies as data points of the radial segment change from tumor, to tumor-involved tissue, and then to normal surrounding tissue. One having skill in the art will appreciate that in some embodiments, plotting signal intensity along each radial segment as a function of distance may be done computationally without actually creating a physical or graphical plot.

Figure 9:
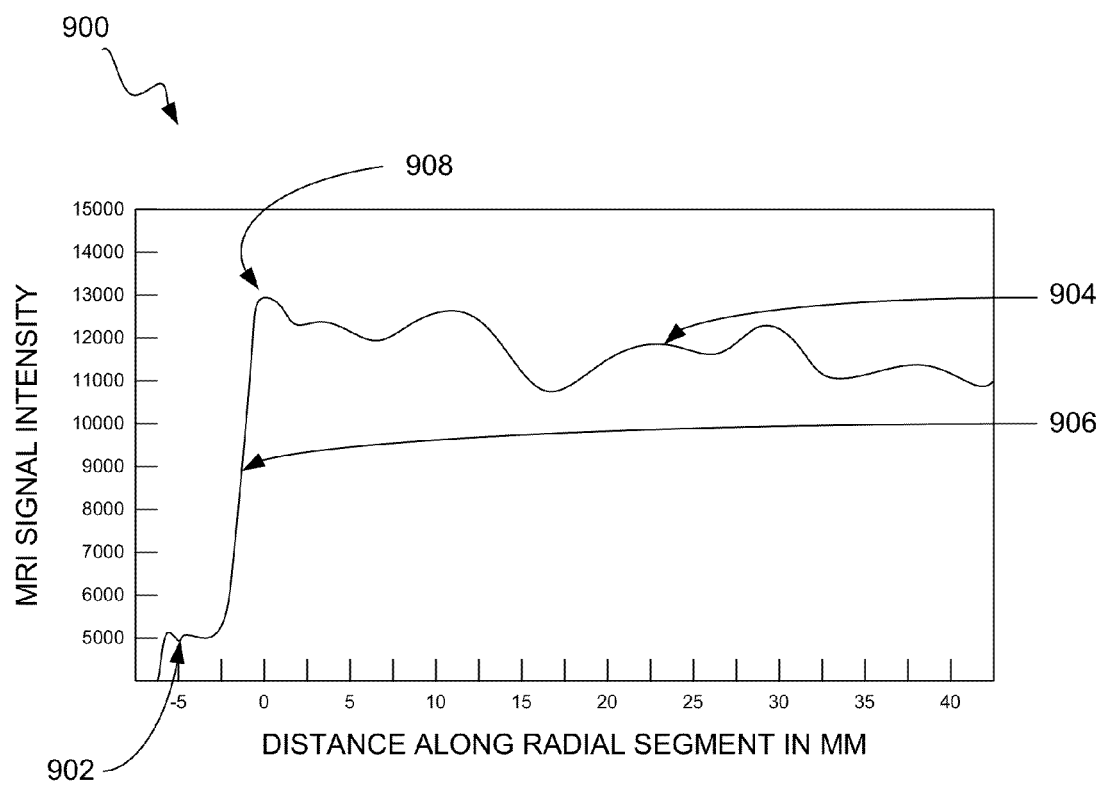
FIG. 9 shows data points indicating MRI signal intensity that correspond to a radial segment plotted as a function of distance along the radial segment.

FIG. 9 depicts an illustrative plot 900 in which the signal intensity data points of a radial segment are plotted as a function of distance along the radial segment. The tumor boundary is located at distance 0 on plot 900. The plot can be divided into two portions. The first portion 902 has relatively low signal intensities which may indicate normal surrounding tissue. The second portion 904 has relatively high signal intensities which may indicate a tumor. Between these two regions is a transitional region 906 which may indicate tumor-involved tissue.

In some embodiments, an average rate in change in signal intensity over the radial segment may be determined from the data points indicating signal intensity. Each rate of change may be defined as the signal intensity change for one pixel distance along the radial segment. These rates of change may be averaged. The average rate in change in signal intensity over the radial segment may related to the biological and/or biophysical properties of tumor water as compared with water in normal tissue at the tumor boundary.

In some embodiments, the average rate in change in signal intensity over the radial segment may be determined from the data points that are within a predetermined distance from the tumor boundary. In some embodiments, the predetermined distance represents a surgical margin of error. For example, one centimeter may be the surgical margin of error, and therefore, the average rate in change in signal intensity over the radial segment may be calculated from the data points that are within one centimeter from the tumor boundary. Referring to FIG. 9, data points that are within one centimeter from the tumor boundary often fully or partially overlap transitional region 906.

In further embodiments, a maximum rate in change in signal intensity over the radial segment may be determined from the data points indicating signal intensity. The maximum rate in change in signal intensity over the radial segment may indicate abrupt changes in tumor water. In some embodiments, the maximum rate in change in signal intensity over the radial segment may be calculated from the data points that are within a predetermined distance from the tumor boundary, as described above. Referring to FIG. 9, the maximum rate in change of signal intensity is often in transitional region 906.

In some embodiments, a normalized signal intensity at the tumor boundary may be determined from the data points indicating signal intensity. The normalized signal intensity at the tumor boundary indicates the maximum signal intensity relative to the signal intensity of the surrounding tissue. The normalized signal intensity at the tumor boundary may indicate tumor boundary biophysical water properties. In some embodiments, the normalized signal intensity at the tumor boundary may be calculated from the data points that are within a predetermined distance from the tumor boundary, as described above.

FIG. 9 also depicts illustrative normalized signal intensity 908. In FIG. 9, normalized signal intensity 908 is the maximum signal intensity within one centimeter of the tumor boundary.

In some embodiments, a distance from the tumor boundary to the maximum signal intensity within a predetermined distance from the tumor boundary may be determined. This parameter may be referred to as the boundary distance. The boundary distance may indicate spatial properties of the tumor boundary.

Each of the above-described tumor boundary parameters may be determined for each of the determined radial segments. In some embodiments, the determined parameters may be statistically analyzed. For example, the parameters may be averaged. In addition, a standard deviation may be determined. The minimum and maximum values may be determined as well. Other statistical measurements are possible as well.

One, all, or any combination of the above-described tumor boundary parameters may be determined. In some embodiments, additional tumor boundary parameters may also be calculated from the data points indicating signal intensity.

i. Determining Respective Tumor Boundary Parameters in the First Study

Referring to the first study described above, the results of four MRI tumor boundary parameters and histopathology parameters for the twenty subjects in the first study is shown in Table 2, as follows:

TABLE 2

MRI Tumor Boundary Parameters and Pathology From Twenty Subjects

| Subject No. | Rate of Change | Max Rate of Change | Boundary Distance | Signal Intensity | Border Type | Margin Status | Diagnosis |
|---|---|---|---|---|---|---|---|
| 1 | 0.21 | 1.46 | 6.38 | 3.63 | infiltrative | positive | serous carcinoma |
| 2 | 0.08 | 0.69 | 5.40 | 1.91 | infiltrative | positive | leiomysarcoma |
| 3 | 0.28 | 1.50 | 8.50 | 4.31 | infiltrative | negative | synovial sarcoma |
| 4 | 0.11 | 0.59 | 7.67 | 2.18 | infiltrative | positive | leiomyosarcoma |
| 5 | 0.06 | 2.24 | 5.15 | 2.99 | infiltrative | positive | alveolar |
| 6 | 0.19 | 1.15 | 7.84 | 3.28 | infiltrative | positive | rhabdomyosarcoma |
| 7 | 0.27 | 1.17 | 7.91 | 4.18 | encapsulated | marginal | pleomorphic sarcoma |
| 8 | 0.05 | 0.51 | 4.95 | 1.72 | encapsulated | positive | liposarcoma |
| 9 | 0.31 | 1.61 | 8.16 | 4.57 | infiltrative | marginal | osteosarcoma |
| 10 | 0.24 | 1.43 | 8.75 | 3.95 | infiltrative | negative | desmoplastic round cell |
| 11 | 0.20 | 0.99 | 8.72 | 3.10 | encapsulated | negative | chondrosarcoma |
| 12 | 0.17 | 0.98 | 7.34 | 3.43 | infiltrative | positive | Ewing's sarcoma |
| 13 | 0.38 | 2.79 | 7.18 | 5.75 | infiltrative | positive | pleomorphic sarcoma |
| 14 | 0.22 | 1.31 | 7.54 | 3.74 | infiltrative | negative | myxofibrosarcoma |
| 15 | 0.37 | 1.09 | 8.74 | 4.98 | infiltrative | negative | synovial sarcoma |
| 16 | 0.32 | 2.39 | 6.99 | 5.70 | encapsulated | negative | pleomorphic sarcoma |
| 17 | 0.12 | 0.86 | 7.50 | 2.60 | encapsulated | negative | pleiomorphic sarcoma |
| 18 | 0.20 | 2.15 | 7.02 | 3.74 | infiltrative | positive | leiomysarcoma |
| 19 | 0.17 | 1.44 | 6.23 | 3.08 | encapsulated | positive | spindle cell sarcoma |
| 20 | 0.08 | 0.77 | 6.41 | 2.33 | infiltrative | positive | myxofibrosarcoma |
| Mean | 0.20 | 1.36 | 7.22 | 3.56 | | | |
| Std. Dev. | 0.10 | 0.62 | 1.17 | 1.14 | | | |

TABLE 2-continued

MRI Tumor Boundary Parameters and Pathology From Twenty Subjects

| Subject No. | Rate of Change | Max Rate of Change | Boundary Distance | Signal Intensity | Border Type | Margin Status | Diagnosis |
|---|---|---|---|---|---|---|---|

In Table 2 above, the rate of change and maximum rate of change parameters are in units of signal intensity per millimeter (mm). Boundary distance is also in mm. Signal intensity is the signal intensity at the tumor boundary and is units of MR signal intensity normalized to the reference tissue signal (tumor signal divided by the reference signal). Marginal refers to a margin status where the tumor approaches to within 1-2 mm of the resection margin.

ii. Determining Respective Tumor Boundary Parameters in the Second Study

Referring to the second study described above, the results of four MRI tumor boundary parameters for included subjects in the second study is shown in Table 3, as follows:

TABLE 3

MRI Tumor Boundary Parameters From Thirty Two Subjects

| Parameter | N | Min | 1st Quartile | Median | Mean | 3rd Quartile | Max |
|---|---|---|---|---|---|---|---|
| Tumor Size | 28 | 0.54 | 9.00 | 17.00 | 332.10 | 269.10 | 3472.00 |
| Age | 31 | 18.00 | 33.50 | 46.00 | 45.30 | 57.50 | 73.00 |
| Rate of Change | 31 | 0.05 | 0.15 | 0.20 | 0.24 | 0.30 | 0.76 |
| Max Rate of Change | 31 | 0.71 | 0.94 | 1.18 | 1.24 | 1.32 | 2.95 |
| Boundary Distance | 31 | 4.95 | 6.54 | 7.50 | 7.28 | 7.91 | 8.75 |
| Signal Intensity | 31 | 1.72 | 3.03 | 3.70 | 4.24 | 4.77 | 13.20 |

In Table 3 above, tumor size refers is in units of centimeters cubed. The rate of change and maximum rate of change parameters are in units of signal intensity per mm. Boundary distance is also in mm. Signal intensity is the signal intensity at the tumor boundary and is units of MR signal intensity normalized to the reference tissue signal (tumor signal divided by the reference signal).

d. Determine Tumor Margin Based on the Determined Tumor Boundary Parameters

At block 308, the computing device determines a tumor margin based on the one or more determined tumor boundary parameters. In some circumstances, the goal of determining a tumor margin is to determine a negative, or tumor free, margin. However, in other circumstances, the tumor margin may not be completely negative (i.e. marginal) in order to balance other surgical considerations, such as the desire to avoid amputation, with the desire to have a negative tumor margin. In some circumstances, the determined boundary parameters may assist in determining a tumor margin that balances the surgical considerations.

In some embodiments, the determined tumor boundary parameters for each radial segment may be used to determine a tumor margin point along the respective radial segment. The respective tumor margin points for each radial segments may be connected to form the determined tumor margin.

In some embodiments, the maximum rate in change in signal intensity may indicate the tumor margin. A maximum rate in change in signal intensity may be determined for each radial segment. The point along the radial segment at which the maximum rate in change in signal intensity occurs may be the tumor margin point. Or, the tumor margin point may be a point along the radial segment at which the signal intensity crosses below a threshold. The threshold may be determined from the signal intensity of the surrounding tissue. For example, the average and standard deviation signal intensity of the surrounding tissue may be determined and used to determine the tumor margin point.

The determination of maximum rate in change in signal intensity may be repeated for each radial segment to determine a tumor margin point for each radial segment. The tumor margin points for each radial segment may be connected to determine the tumor margin.

Figure 6:
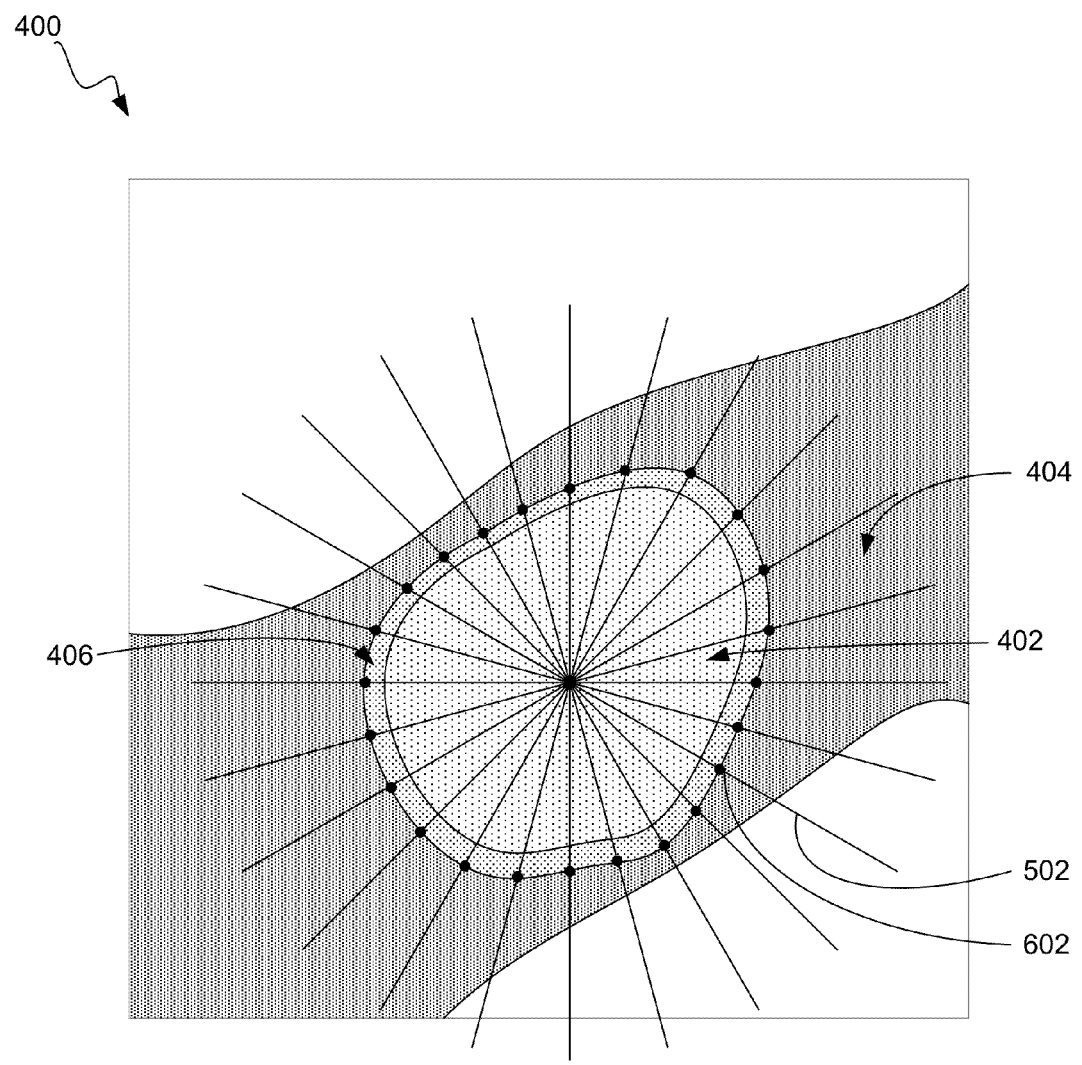
FIG. 6 shows illustrative radial segments and illustrative tumor boundary characteristics overlaid onto an MR image of a tumor and surrounding tissue.

FIG. 6 depicts illustrative imaging data 400 that shows the sarcoma 402, surrounding tissue 404, and tumor-involved surrounding tissue 406, as described in FIG. 4. In addition, FIG. 6 depicts a determined boundary parameter 602 that indicates the maximum rate in change in signal intensity. Boundary parameter 602 is overlaid on the imaging data 400 at the point along the radial segment 502 at which the maximum rate in change in signal intensity occurs, as shown. Additional boundary parameters indicating the maximum rate in change in signal intensity are also overlaid on the imaging data 400 at the each respective point along each radial segment at which the maximum rate in change in signal intensity occurs, as shown.

Although the example above describes determining the tumor margin based on the maximum rate of change of each radial segment, the tumor margin may be determined based on any of the tumor boundary parameters, or any combination of tumor boundary parameters. For example, a tumor margin may be based on the maximum rate of change of each radial segment, but be adjusted by the normalized signal intensity at the tumor boundary, among many other examples.

i. Determining Tumor Margin in the First Study

In the first study, the ability of the tumor boundary parameters to differentiate positive from negative margins was tested via a non-parametric rank test by taking histopathologic data from 20 patients and correlating with the MR tumor boundary parameters. The individual values of the tumor boundary parameters were each ranked and a boxplot was generated to compare the ranks of cases with positive margins versus those with negative ones. The p-values are based on the (non-parametric) rank test.

Figure 11:
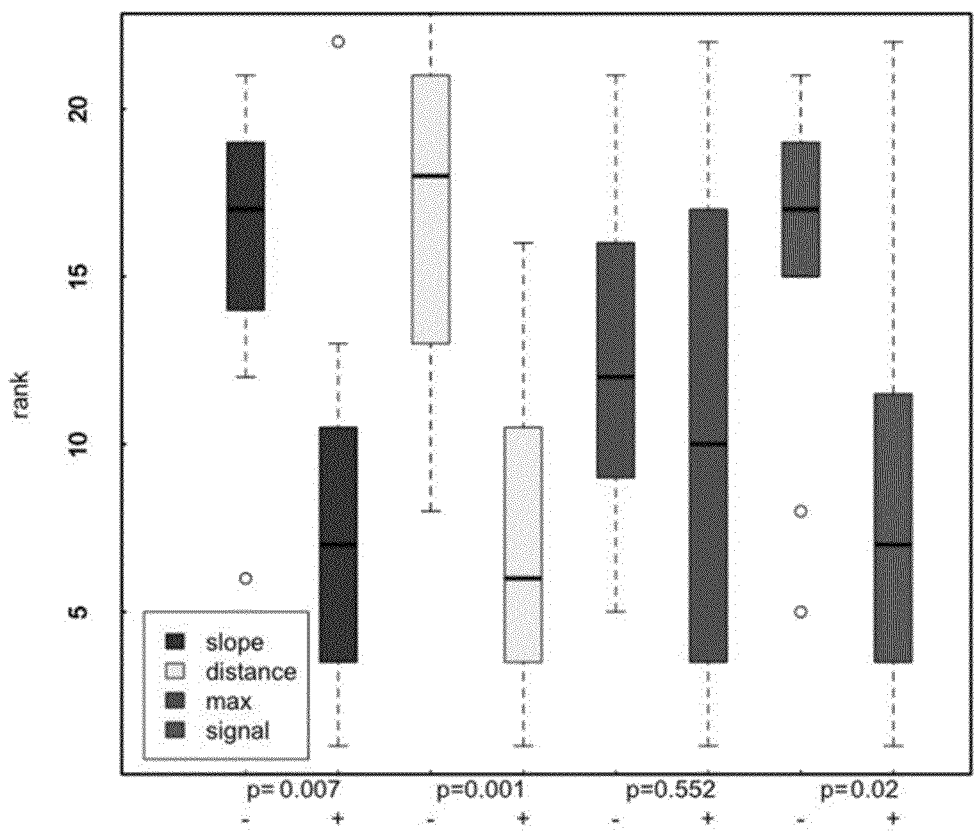
FIG. 11 shows a boxplot that compare the ranks of subjects having resected tumors with positive margins versus those with negative ones in a first study.

The boxplot is shown in FIG. 11. In FIG. 11, slope refers to the rate of change. Distance refers to boundary distance. Max refers to maximum rate of change. Signal refers to normalized signal intensity at the tumor boundary. The parameters slope, distance, max, and signal appear on the plot from left to right, respectively. The dark line in the middle of each plot indicates the median. The dotted portions of each plot indicate the minimum and maximum of the parameters.

ii. Determining Tumor Margin in the Second Study

In the second study, p-values for the tumor boundary parameters were determined. The results are in Table 4, as follows:

TABLE 4

| Parameter | N | p-value |
| --- | --- | --- |
| Rate of Change | 31 | 0.355 |
| Max Rate of Change | 31 | 0.983 |
| Boundary Distance | 31 | 0.012 |
| Signal Intensity | 31 | 0.527 |

In some embodiments, the risk of tumor recurrence may be predicted based on the one or more determined tumor boundary parameters. More particularly, in some embodiments, the local and metastatic risk of tumor recurrence may be predicted based on the one or more determined tumor boundary parameters. A set of tumor boundary parameters may be determined for multiple patients. The outcome of each patient may be correlated to the respective tumor boundary parameters. Using these accumulated determined tumor boundary parameters that are correlated to patient outcome, the risk of tumor recurrence for a patient currently diagnosed with cancer may be determined based on the patient's tumor boundary parameters.

Patients identified by the methods of the invention as at an increased risk of tumor recurrence may be treated more aggressively to limit the risk of recurrence, including but not limited to chemotherapy and/or radiation therapy prior to or following tumor removal, as deemed most appropriate by an attending physician based on all relevant factors for an individual patient. For example, identification of an increased risk of tumor recurrence may cause a physician to treat with pre-or-post-or intra-operative radiation therapy. In some circumstances, accurate identification of a tumor at less risk for recurrence may suggest that less surrounding tissues may be removed. In some cases, such as where the tumor is located in the abdomen, removing less surrounding tissue may result in a greater organ function after surgery, since less surrounding tissue was removed during surgery.

Figure 12:
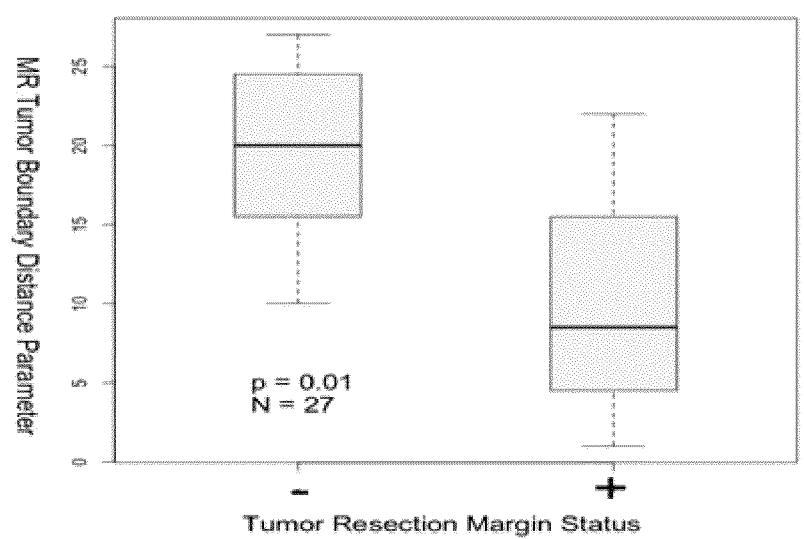
FIG. 12 shows a boxplot that compares boundary distance to histological margin status in a second study.

In the second study, a boxplot was generated that compares boundary distance to histological margin status graphically. The model suggests that the boundary distance parameter is related to histological margin status (p=0.01). The boxplot is shown in FIG. 12. A logical regression was used to quantify the relationship shown in FIG. 12 between boundary distance and histological margin status. This data is shown in Table 5.

TABLE 5

| Parameter | Coefficient | p-value |
| --- | --- | --- |
| Intercept | .26 | .62 |
| Boundary Distance | −2.3 | .01 |

The data in FIG. 12 and Table 5 suggests that the boundary distance parameter may act as surrogate marker for histological margin status prior to surgery in order to assess prognosis.

e. Cause Graphical Representation of Determined Tumor Margin to be Displayed on a Graphical Display At block 310, the computing device causes a graphical representation of the determined tumor margin to be displayed on a graphical display. For example, computing device 100 of FIG. 1 may cause a graphical representation of the determined tumor margin to be displayed on graphical display 122. Causing a graphical representation of the determined tumor margin to be displayed on a graphical display may assist a user, such as a surgeon, in planning or performing tumor resection surgery.

In some embodiments, causing a graphical representation of the determined tumor margin to be displayed on a graphical user interface involves causing the graphical representation of the determined tumor margin to be overlaid over the image of the tumor and the surrounding one or more tissues. This arrangement may display the determined tumor margin to the surgeon during the planning or performance of tumor resection surgery.

Figure 7:
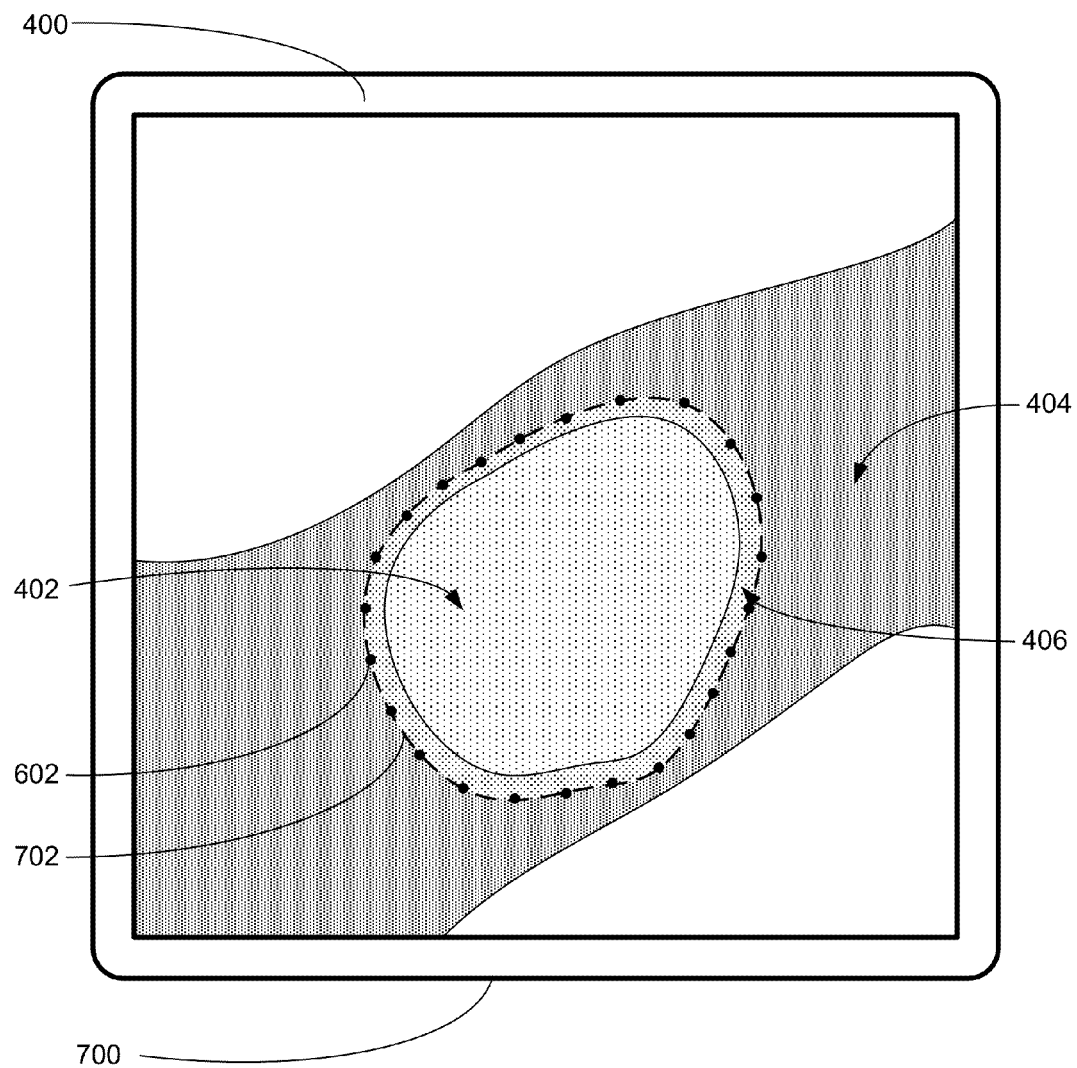
FIG. 7 shows an illustrative graphical representation of a tumor margin displayed on a graphical display.

FIG. 7 depicts imaging data 400 displayed on graphical display 700. Imaging data 400 shows sarcoma 402, surrounding tissue 404, and tumor-involved surrounding tissue 406. Graphical display 700 may be implemented in computing device 100 as graphical display 122.

FIG. 7 also depicts the determined tumor margin 702 as displayed on graphical display 700. In FIG. 7, the determined tumor margin 702 is overlaid over sarcoma 402, surrounding tissue 404, and tumor-involved surrounding tissue 406.

In some embodiments, the computing device causes a surgical instrument to move based on the determined tumor margin. For example, the computing device may cause a computer-assisted surgical instrument to move based on the determined tumor margin. Or, the computing device may cause a robotic surgical instrument to move based on the determined tumor margin. Such instruments may be configured to assist in tumor resection. In some embodiments, the imaging data includes in vivo imaging data for a patient, and the computing device causes a surgical instrument to move based on the determined tumor margin.

In some embodiments, the determined tumor margin may indicate physical coordinates. The surgical instrument may move according to the physical coordinates. The surgical instrument may move along the determined tumor margin to assist in resecting the tumor along the determined tumor margin.

In some embodiments, causing a surgical instrument to move based on the determined tumor margin involves sending data indicating tumor margin coordinates to a surgical instrument. For example, computing device 100 in FIG. 1 may send the data indicating tumor margin coordinates over system bus, network, or other connection mechanism 112. In such embodiments, the data indicating tumor margin coordinates may be arranged to cause a surgical instrument to move based on the determined tumor margin. Other examples are possible as well.

3. Conclusion

While various aspects and embodiments have been disclosed herein, other aspects and embodiments will be apparent to those skilled in the art. For example, with respect to the flow charts depicted in the figures and discussed herein, functions described as blocks may be executed out of order from that shown or discussed, including substantially concurrent or in reverse order, depending on the functionality involved. Further, more or fewer blocks and/or functions may be used and/or flow charts may be combined with one another, in part or in whole.

The various aspects and embodiments disclosed herein are for purposes of illustration and are not intended to be limiting, with the true scope and spirit being indicated by the following claims. Other embodiments can be utilized, and other changes can be made, without departing from the spirit or scope of the subject matter presented herein.

We claim:

1. A computer-implemented method comprising:
  receiving imaging data, wherein the imaging data indicates a tumor and one or more tissues that surround the tumor;
  determining one or more radial segments that extend from the tumor to the one or more surrounding tissues based on the imaging data, wherein the one or more radial segments each comprise one or more respective data points indicating signal intensity;

determining one or more respective tumor boundary parameters for each of the one or more radial segments based on at least the one or more respective data points indicating signal intensity, wherein each of the one or more radial segments intersect a tumor boundary;

based on the one or more determined tumor boundary parameters, determining a tumor margin that is outside of the tumor boundary and at least partially within a transition region between the tumor boundary and the one or more tissues that surround the tumor, wherein the determined tumor margin represents a surface along which the tumor is to be resected during surgery; and causing a graphical representation of the determined tumor margin to be displayed on a graphical display.

2. The method of claim 1, wherein determining the one or more respective tumor boundary parameters for each of the one or more radial segments comprises:

determining, for each of the one or more respective radial segments, at least one of: (i) an average rate in change in signal intensity over the radial segment, (ii) a maximum rate in change in signal intensity over the radial segment, (iii) a normalized signal intensity at the tumor boundary; or (iv) a distance from the tumor boundary to the maximum signal intensity along the tumor margin within a predetermined distance.

3. The method of claim 2, further comprising:
determining a degree of irregularity of the tumor boundary; and
determining a number of the one or more radial segments based on the determined degree of irregularity of the tumor boundary.

4. The method of claim 1, wherein determining the one or more respective tumor boundary parameters for each of the one or more radial segments comprises determining respective maximum rates of change of signal intensity over the one or more respective radial segments within a threshold distance outside of the tumor boundary.

5. The method of claim 1, further comprising:
before determining the one or more radial segments, defining a tumor reference point that is indicative of a center of the tumor based on the imaging data.

6. The method of claim 1, wherein the imaging data comprises at least one T2-weighted MRI image.

7. The method of claim 1, further comprising:
predicting the risk of tumor recurrence based on the one or more determined tumor boundary parameters.

8. The method of claim 1,
wherein receiving the imaging data comprises receiving, from an image-sensing surgical instrument, in vivo imaging data depicting a tumor and one or more surrounding tissues during surgery; and
wherein causing a graphical representation of the determined tumor margin to be displayed on a graphical user interface comprises causing the graphical representation of the determined tumor margin to be overlaid over the in vivo imaging data depicting the tumor and the surrounding one or more tissues during surgery.

9. The method of claim 1, wherein the imaging data comprises in vivo imaging data for a patient, further comprising:
causing a surgical instrument to move based on the determined tumor margin.

10. The method of claim 1, wherein determining the one or more respective tumor boundary parameters for each of the one or more radial segments comprises:

determining respective normalized signal intensities at the tumor boundary along the one or more radial segments.

11. The method of claim 1, wherein determining the one or more respective tumor boundary parameters for each of the one or more radial segments comprises:

determining respective distances along the one or more radial segments from the tumor boundary to the maximum signal intensity within a predetermined distance from the tumor boundary.

12. A non-transitory computer readable medium having stored therein instructions executable by a computing device to cause the computing device to perform functions comprising:

receiving imaging data, wherein the imaging data indicates a tumor and one or more tissues that surround the tumor;

determining one or more radial segments that extend from the tumor to the one or more surrounding tissues based on the imaging data, wherein the one or more radial segments each comprise one or more respective data points indicating signal intensity;

determining one or more respective tumor boundary parameters for each of the one or more radial segments based on at least the one or more respective data points indicating signal intensity, wherein each of the one or more radial segments intersect a tumor boundary;

based on the one or more determined tumor boundary parameters, determining a tumor margin that is outside of the tumor boundary and at least partially within a transition region between the tumor boundary and the one or more tissues that surround the tumor, wherein the determined tumor margin represents a surface along which the tumor is to be resected during surgery; and causing a graphical representation of the determined tumor margin to be displayed on a graphical display.

13. The non-transitory computer readable medium of claim 12, wherein determining the one or more respective tumor boundary parameters for each of the one or more radial segments comprises:

determining, for each of the one or more respective radial segments, at least one of: (i) an average rate in change in signal intensity over the radial segment, (ii) a maximum rate in change in signal intensity over the radial segment, (iii) a normalized signal intensity at the tumor boundary; or (iv) a distance from the tumor boundary to the maximum signal intensity along the tumor margin within a predetermined distance.

14. The non-transitory computer readable medium of claim 12, wherein determining the one or more respective tumor boundary parameters for each of the one or more radial segments comprises determining respective maximum rates of change of signal intensity over the one or more respective radial segments within a threshold distance outside of the tumor boundary.

15. The non-transitory computer readable medium of claim 12, wherein the instructions are further executable to cause the computing device to perform functions comprising:
before determining the one or more radial segments, defining a tumor reference point that is indicative of a center of the tumor based on the imaging data.

16. The non-transitory computer readable medium of claim 12, wherein the imaging data comprises at least one T2-weighted MRI image.

17. The non-transitory computer readable medium of claim 12, wherein the instructions are further executable to cause the computing device to perform functions comprising:
predicting the risk of tumor recurrence based on the one or more determined tumor boundary parameters.

18. The non-transitory computer readable medium of claim 12, wherein receiving the imaging data comprises receiving, from an image-sensing surgical instrument, in vivo imaging data depicting a tumor and one or more surrounding tissues during surgery; and wherein causing a graphical representation of the determined tumor margin to be displayed on a graphical user interface comprises causing the graphical representation of the determined tumor margin to be overlaid over the in vivo imaging data depicting the tumor and the surrounding one or more tissues during surgery.

19. The non-transitory computer readable medium of claim 12, wherein the instructions are further executable to cause the computing device to perform functions comprising:

determining a degree of irregularity of the tumor boundary; and determining a number of the one or more radial segments based on the determined degree of irregularity of the tumor boundary.

20. The non-transitory computer readable medium of claim 12, wherein the imaging data comprises in vivo imaging data for a patient, wherein the instructions are further executable to cause the computing device to perform functions comprising:

causing a surgical instrument to move based on the determined tumor margin.

21. The non-transitory computer readable medium of claim 12, wherein determining the one or more respective tumor boundary parameters for each of the one or more radial segments comprises:

determining respective normalized signal intensities at the tumor boundary along the one or more radial segments.

22. The non-transitory computer readable medium of claim 12, wherein determining the one or more respective tumor boundary parameters for each of the one or more radial segments comprises:

determining respective distances along the one or more radial segments from the tumor boundary to the maximum signal intensity within a predetermined distance from the tumor boundary.

23. A computing device comprising:

a display;

a non-transitory computer readable medium; and program instructions stored on the non-transitory computer readable medium and executable by at least one processor to:

receive imaging data, wherein the imaging data indicates a tumor and one or more tissues that surround the tumor;

determine one or more radial segments that extend from the tumor to the one or more surrounding tissues based on the imaging data, wherein the one or more radial segments each comprise one or more respective data points indicating signal intensity;

determine one or more respective tumor boundary parameters for each of the one or more radial segments based on at least the one or more respective data points indicating signal intensity, wherein each of the one or more radial segments intersect a tumor boundary;

based on the one or more determined tumor boundary parameters, determining a tumor margin that is outside of the tumor boundary and at least partially within a transition region between the tumor boundary and the one or more tissues that surround the tumor, wherein the determined tumor margin represents a surface along which the tumor is to be resected during surgery; and cause a graphical representation of the determined tumor margin to be displayed on a graphical display.

24. The computing device of claim 23, wherein determining the one or more respective tumor boundary parameters for each of the one or more radial segments comprises:

determining, for each of the one or more respective radial segments, at least one of: (i) an average rate in change in signal intensity over the radial segment, (ii) a maximum rate in change in signal intensity over the radial segment, (iii) a normalized signal intensity at the tumor boundary; or (iv) a distance from the tumor boundary to the maximum signal intensity along the tumor margin within a predetermined distance.

25. The computing device of claim 23, wherein determining the one or more respective tumor boundary parameters for each of the one or more radial segments comprises determining respective maximum rates of change of signal intensity over the one or more respective radial segments within a threshold distance outside of the tumor boundary.

26. The computing device of claim 23, wherein the program instructions are further executable by at least one processor to:

before determining the one or more radial segments, define a tumor reference point that is indicative of a center of the tumor based on the imaging data.

27. The computing device of claim 23, wherein the imaging data comprises at least one T2-weighted MRI image.

28. The computing device of claim 23, wherein the program instructions are further executable by at least one processor to:

predict the risk of tumor recurrence based on the one or more determined tumor boundary parameters.

29. The computing device of claim 23, wherein receiving the imaging data comprises receiving, from an image-sensing surgical instrument, in vivo imaging data depicting a tumor and one or more surrounding tissues during surgery; and wherein causing a graphical representation of the determined tumor margin to be displayed on a graphical user interface comprises causing the graphical representation of the determined tumor margin to be overlaid over the in vivo imaging data depicting the tumor and the surrounding one or more tissues during surgery.

30. The computing device of claim 23, wherein the program instructions are further executable by at least one processor to:

determine a degree of irregularity of the tumor boundary; and determine a number of the one or more radial segments based on the determined degree of irregularity of the tumor boundary.

31. The computing device of claim 23, wherein the imaging data comprises in vivo imaging data for a patient, and wherein the program instructions are further executable by at least one processor to:

cause a surgical instrument to move based on the determined tumor margin.

32. The computing device of claim 23, wherein determining the one or more respective tumor boundary parameters for each of the one or more radial segments comprises:

determining respective normalized signal intensities at the tumor boundary along the one or more radial segments.

33. The computing device of claim 23, wherein determining the one or more respective tumor boundary parameters for each of the one or more radial segments comprises:

determining respective distances along the one or more radial segments from the tumor boundary to the maximum signal intensity within a predetermined distance from the tumor boundary.

\* \* \* \* \*